United States Patent [19]

Parker

[11] 4,197,853
[45] Apr. 15, 1980

[54] PO2/PCO2 SENSOR

[75] Inventor: Dawood Parker, London, England

[73] Assignee: G. D. Searle & Co., Skokie, Ill.

[21] Appl. No.: 926,473

[22] Filed: Jul. 20, 1978

[30] Foreign Application Priority Data

Jul. 26, 1977 [GB] United Kingdom ............... 31273/77

[51] Int. Cl.² ............................................... A61B 5/00
[52] U.S. Cl. ................................. 128/635; 204/195 B
[58] Field of Search .................... 128/635; 204/195 B, 204/195 P

[56] References Cited

U.S. PATENT DOCUMENTS

| | | | |
|---|---|---|---|
| 3,659,586 | 5/1972 | Johns et al. ........................... | 128/635 |
| 3,795,239 | 3/1974 | Eberhard et al. ..................... | 128/635 |

OTHER PUBLICATIONS

"A Single-Unit Carbon Dioxide Sensing Microelectrode System," by Van Kempien & Kreuzer; Respiration Physiology, (1975), 23, 371-379.

Primary Examiner—Willis Little
Attorney, Agent, or Firm—John A. Dhuey

[57] ABSTRACT

This invention relates to an electrochemical sensor system for the simultaneous and continuous measurement of the partial pressure of oxygen PO2 and carbon dioxide partial pressure PCO2 in fluids. The electrochemical sensor of the present invention is particularly useful for intra-arterial measuring PCO2 and PO2 in blood and is readily adapted to transcutaneous measurement of these blood gases by the addition of a heating element and minor configurational changes.

10 Claims, 3 Drawing Figures

$PO_2/PCO_2$ SENSOR

BACKGROUND OF THE INVENTION

Conventional $PO_2$ sensors comprise a pair of metal electrodes electrically connected by an electrolyte and encased in an oxygen permeable membrane in contact with the electrolyte and with the fluid to be examined. One electrode, the cathode, is of a metal capable of the electrochemical reduction of oxygen passing through the membrane so producing a current related to the oxygen partial pressure in the fluid.

Conventional $PCO_2$ sensors also comprise a pair of electrodes, an electrolyte and a membrane, in this case permeable to carbon dioxide. The sensor functions by recording the effect of the change in pH resulting from the passage of carbon dioxide and water through the membrane, its dissolution to form carbonic acid and the dissociation of carbonic acid, liberating hydrogen ions according to the equation:

$$CO_2 + H_2O \rightarrow H_2CO_3$$

$$H_2CO_3 \rightarrow H^+ + HCO_3^-$$

A single unit carbon dioxide-oxygen sensing microelectrode system is disclosed in Respiration Physiology 23 371-379 (1975). This system involves a platinum cathode and a silver-silver chloride anode in quinhydrone/potassium chloride electrolyte. This system can be used to measure $PCO_2$ and $PO_2$ independently, but not simultaneously.

SUMMARY OF THE INVENTION

The present invention encompasses
An electrochemical sensor for the simultaneous and continuous measurement of $PO_2$ and $PCO_2$ in fluids which comprises:

(a) an electrode chamber having within: a first electrode responsive to pH changes produced by the presence of carbon dioxide, a second electrode capable of electrochemically reducing oxygen.

a reference electrode for each of, or common to, the first and second electrodes, means for holding first electrode, second electrode and reference electrode in spaced apart, insulated relationship, and electrolyte, preferably an alkaline electrolyte, in contact with the reference electrode and first and second electrodes and (b) a membrane permeable to oxygen and carbon dioxide having first and second side, the first side being in contact with the electrolyte and the second side available for exposure to carbon dioxide and oxygen gases from fluid to be tested, said membrane holding the alkaline electrolyte in contact with the electrodes and providing for entry of oxygen and carbon dioxide gas into the electrolyte, said membrane also being permeable to water when the electrolyte is in solid form.

Means for simultaneously measuring electrical changes produced by carbon dioxide between the first electrode and the reference electrode and by oxygen between the second electrode and the reference electrode are connected to the respective electrodes.

In one embodiment the sensor is adapted for mounting on the tip of an intra-arterial catheter for measurement of $PO_2$ and $PCO_2$ in blood. The electrode responsive to changes in carbon dioxide is a pH glass electrode; the electrode for electrochemically reducing oxygen is made from silver or platinum and the reference electrode is silver/silver chloride, the membrane is water, carbon dioxide and oxygen permeable polystyrene; and the electrolyte is a dried or semi-solid layer derived from an aqueous solution of sodium bicarbonate and potassium chloride.

The membrane preferably made from a biologically inert polymer is permeable to carbon dioxide and oxygen. If a solid electrolyte is used the membrane must also be water permeable. A suitable membrane is prepared by dip-coating electrolyte coated sensor with $CO_2/O_2/H_2O$ permeable polystyrene membrane. In producing the sensor in this form the electrodes are first assembled in the catheter tip which is then coated with a solid slectrolyte which is in turn dip-coated with an $O_2/CO_2/H_2O$ permeable membrane, both coatings completely covering the electrodes.

In another embodiment the carbon dioxide and oxygen permeable membrane is arranged to be placed in contact with or in proximity to the skin so that carbon dioxide and oxygen can pass from the blood through the skin, through the membrane and into the electrolyte.

This latter embodiment is advantageously equipped with a controlled heating element (i.e. controlled with a thermistor) whereby the sensor is heated to and maintained at a temperature suitable to increase blood flow in that area of the skin in contact with the sensor.

Thus, an important embodiment of the present invention is a transcutaneous sensor which can measure $PO_2$ and $PCO_2$ through the skin by determining the $PO_2$ and $PCO_2$ of gases diffusing through the skin. One example of such a modification of the sensor of the invention is a pH glass $CO_2$ electrode surrounded by an annular reference electrode incorporating one or more silver $O_2$ electrodes and a controlled heating element to increase blood flow in the area of the skin where the measurement is taken. The exposed faces of the electrodes are in contact with a suitable electrolyte, which can be liquid and less rigorous sterilization procedures can be used for the device than are necessary for the intra-arterial embodiment. Finally, the electrolyte is covered by an $O_2/CO_2$ permeable membrane. Water permeability is not essential if a 'wet' or liquid electrolyte is used. This sensor can be applied directly to the skin which is locally heated by an electrical heating element with thermistor control to increase blood flow and reliable measurements of blood $PO_2$ and $PCO_2$ can be made from gases diffusing through the skin. In all forms of the sensor according to the invention it is preferred that the $CO_2$ electrode and the $O_2$ electrode be separated, at least in part, by the reference electrode to minimize any interference between the hydrogen ions present at the $CO_2$ electrode and the hydroxylions generated at the $O_2$ electrode.

The first electrode responsive to pH changes produced by the presence of carbon dioxide is preferably a pH glass electrode.

The second electrode capable of electrochemically reducing oxygen is made from any material having the required property of electrochemical reduction of oxygen with a polarizing current such as silver, gold, platinum, carbon or suitable semiconductor material.

The reference electrode is preferably silver/silver chloride in block or wound wire form.

The output from electrochemical reduction of oxygen is measured by conventional polarographic circuitry using a polarizing source and current amplifier. The output of the pH glass electrode is measured by a high impedance voltage amplifier. Oxygen and carbon dioxide are measured simultaneously intra-arterially or transcutaneously without interference. Those skilled in the electronic arts will recognize a wide variety of electrical components which will serve as means to measure $CO_2/O_2$ induced changes in the electrodes.

The preferred electrolyte material is one which is alkaline in the unbuffered state and contains free halide ions. The choice of electrolyte is dictated by the choice of materials for the electrodes.

A preferred electrolyte for use with a pH glass $CO_2$ electrode, a silver/silver chloride reference electrode and a silver oxygen electrode is a mixture of $NaHCO_3$ and KCl. The electrolyte may be in 'wet' (liquid) or semi-solid form. Sodium bicarbonate/potassium chloride in ethylene glycol is a suitable alkaline electrolyte for the transcutaneous mode of the present invention.

The transcutaneous form of the sensor described herein can also be used to measure blood $PO_2$ and $PCO_2$ in vitro. In this case the membrane of the sensor is held in contact with a sample of blood and the electrodes measure the partial pressure of oxygen and carbon dioxide diffusing from the blood and through the membrane.

DETAILED DESCRIPTION OF THE INVENTION

Figure 1:
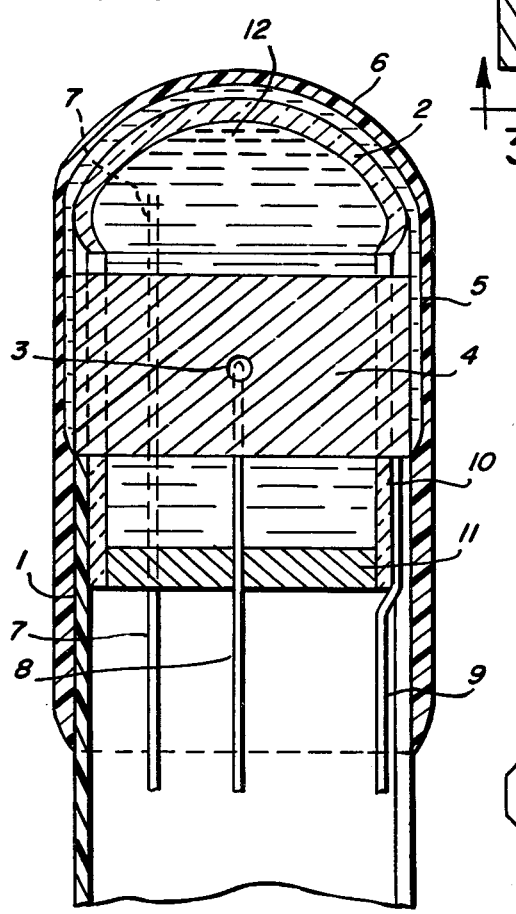
FIG. 1: Cross section of electrochemical sensor for mounting on the tip of a catheter.

Referring now to FIG. 1 of the drawings, the electrochemical sensor is mounted in the tip of a 5F polyvinyl chloride catheter 1. The electrochemical sensor consists of a carbon dioxide sensitive electrode 2 in the form of a pH glass head mounted in the end of the catheter. The electrode for electrochemically reducing oxygen 3 is a 180 um diameter silver wire. Electrodes 2 and 3 are common to a silver/silver chloride reference electrode 4. That area of the catheter carrying the electrodes is covered with a layer of alkaline electrolyte 5 consisting of a semi-solid sodium bicarbonate/potassium chloride electrolyte which in turn is coated with $O_2/CO_2/H_2O$ permeable polystyrene membrane 6. The electrode for reducing oxygen, silver wire 3 is in contact with the alkaline electrolyte layer 5. Conventional electrical connections 7, 8, and 9 extend from the respective electrodes. The pH glass electrode 2 is mounted on a hollow lead glass shaft 10 closed by a silicon rubber seal 11. The lumen of the glass shaft is filled with a chloride ion gelled electrolyte, alternatively an electrically conductive epoxy resin 12. The carbon dioxide responsive electrode 2 and electrode for electrochemically reducing oxygen 3 are 2 to 4 mm apart in this embodiment.

Figure 2:
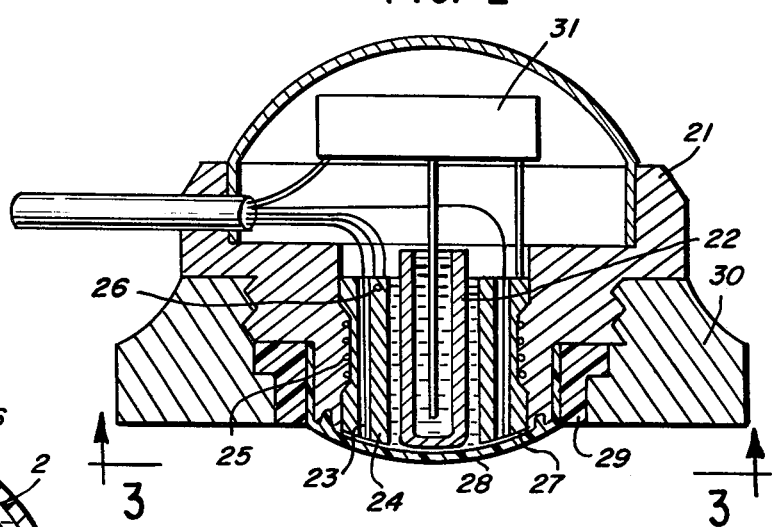
FIG. 2: Cross section of electrochemical sensor for transcutaneous measurement of carbon dioxide and oxygen.

Referring now to FIG. 2, the transcutaneous sensor consists of a sensor body 21 having positioned therein a centrally arranged pH glass electrode 22 for measuring carbon dioxide. Surrounding the pH electrode is an annular silver/silver chloride reference anode 24 and positioned therein and insulated therefrom are two radially opposed platinum oxygen electrodes 23.

The reference anode 24 is provided with a heater 25 the temperature of which is controlled by a thermistor 26 positioned in the reference electrode. The exposed surfaces of the electrodes are in contact with an electrolyte 27 which is a 0.1 molar Na $HCO_3$/0.1 molar KCl solution in ethylene glycol. The electrolyte is retained by an oxygen and carbon dioxide permeable membrane 28 which is held in position by a PTFE ring 29 and a threaded retaining ring 30, thereby sealing the alkaline electrolyte within the electrode chamber and permitting oxygen to pass from the skin of an animal through the membrane into the alkaline electrolyte.

A field effect transistor 31 is provided in effect to lower the impedance of the $CO_2$ electrode. In use the sensor is placed in contact with or in proximity to the skin of the patient and the heater activated to raise the temperature of the skin to a value sufficient to increase blood flow locally. Oxygen and carbon dioxide in the blood diffuse through the skin layer and through the membrane and are detected by the oxygen cathode and the pH glass electrode respectively and the currents suitably recorded.

Figure 3:
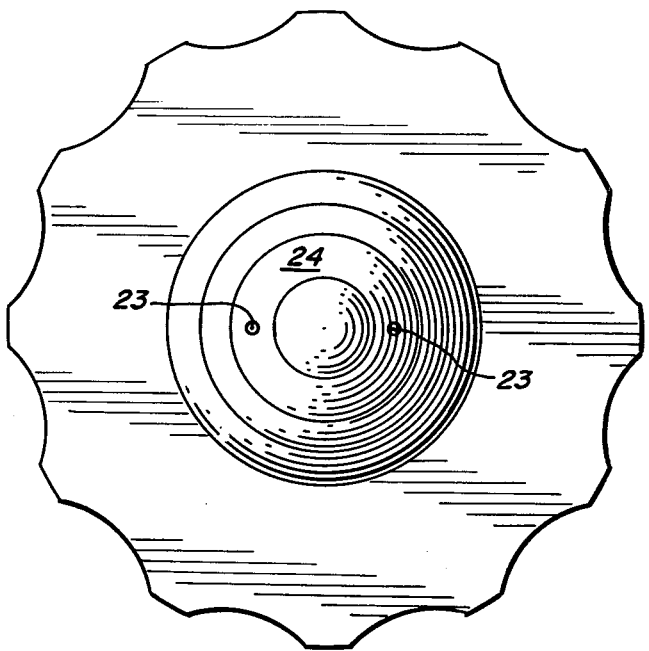
FIG. 3: Plan view of electrochemical sensor for transcutaneous measurement of carbon dioxide and oxygen.

FIG. 3 illustrates the two radially disposed platinum oxygen electrodes 23 within but insulated from the silver/silver chloride reference electrode 24.

What is claimed is:

1. An electrochemical sensor for the simultaneous and continuous measurements of $PO_2$ and $PCO_2$ in fluids which comprises:
   (a) an electrode chamber having within;
   a first electrode responsive to pH changes produced by the presence of carbon dioxide,
   a second electrode capable of electrochemically reducing oxygen.
   a reference electrode for each of or common to the first and second electrodes,
   means for holding first electrode, second electrode and reference electrode in spaced apart, insulated relationship.
   an electrolyte in contact with the reference electrode and first and second electrodes;
   (b) a membrane permeable to oxygen and carbon dioxide having a first and second side, the first side being in contact with the electrolyte and the second side available for exposure to carbon dioxide and oxygen gases from fluid to be tested, said membrane holding the electrolyte in contact with the electrodes and providing for entry of oxygen and carbon dioxide gas into the electrolyte; and said membrane being also permeable to water when the electrolyte is solid.

2. An electrochemical sensor for the simultaneous and continuous measurements of $PO_2$ and $PCO_2$ in fluids which comprises
   (a) an electrode chamber having within: a first electrode responsive to pH changes produced by the presence of carbon dioxide,
   a second electrode capable of electrochemically reducing oxygen,
   a reference electrode for each of or common to the first and second electrodes,
   means for holding first electrode, second electrode and reference electrode in spaced apart, insulated relationship,
   a solid electrolyte in contact with the reference electrode and first and second electrodes;

(b) a membrane permeable to water, oxygen and carbon dioxide having a first and second side, the first side being in contact with the electrolyte and the second side available for exposure to carbon dioxide and oxygen gases from fluid to be tested, said membrane holding the electrolyte within in contact with the electrodes and providing for entry of oxygen and carbon dioxide gas into the electrolyte.

3. An electrochemical sensor for the simultaneous and continuous transcutaneous measurements of $PO_2$ and $PCO_2$ through animal skin which comprises:

(a) an electrode chamber having within;

a first electrode responsive to pH changes produced by the presence of carbon dioxide, a second electrode capable of electrochemically reducing oxygen, a reference electrode for each of or common to the first and second electrodes, means for holding first electrode, second electrode and reference electrode in spaced apart, insulated relationship, an electrolyte in contact with the reference electrode and first and second electrodes;

(b) a membrane permeable to oxygen and carbon dioxide having a first and second side, the first side being in contact with the electrolyte and the second side available for exposure to carbon dioxide and oxygen gases from the animal skin to be tested, said membrane holding the electrolyte in contact with the electrodes and providing for entry of oxygen and carbon dioxide gas into the electrolyte and (c) a controlled heating element associate with the electrode chamber for heating the animal skin in contact with or in proximity to the membrane.

4. An electrochemical sensor, according to claim 1, 2 or 3 wherein the electrolyte is an alkaline electrolyte.

5. An electrochemical sensor, according to claim 1, 2 or 3 in combination with means for simultaneously measuring electrical changes produced by carbon dioxide between the first electrode and the reference electrode and by oxygen between the second electrode and the reference electrode.

6. An electrochemical sensor, according to claims 1, 2 or 3 wherein the first electrode is pH glass electrode.

7. An electrochemical sensor, according to 1, 2 or 3 wherein the second electrode is silver or platinum.

8. An electrochemical sensor, according to claims 1, 2 or 3 wherein the reference electrode is made from silver/silver chloride.

9. An electrochemical sensor, according to claims 1, 2 or 3 wherein the membrane is made of polystyrene.

10. An electrochemical sensor, according to claim 2, mounted in the tip of an intra-arterial catheter for measurement of $PO_2$ and $PCO_2$ in blood.

* * * * *